United States Patent [19]

Afromowitz et al.

[11] Patent Number: 5,275,169

[45] Date of Patent: Jan. 4, 1994

[54] APPARATUS AND METHOD FOR DETERMINING PHYSIOLOGIC CHARACTERISTICS OF BODY LUMENS

[75] Inventors: Martin A. Afromowitz, Mercer Island; Roger A. Wolthuis; Gordon L. Mitchell, both of Woodinville, all of Wash.

[73] Assignee: Innovation Associates, Bellevue, Wash.

[21] Appl. No.: 822,032

[22] Filed: Jan. 15, 1992

[51] Int. Cl.$^5$ ............................................. A61M 29/00
[52] U.S. Cl. ..................................... 128/673; 128/748; 604/97; 604/99; 604/101
[58] Field of Search ............... 128/673, 774, 778, 775, 128/786, 782, 748, 692; 33/511, 512; 604/96-

[56] References Cited

U.S. PATENT DOCUMENTS

| | | | |
|---|---|---|---|
| 4,329,993 | 5/1982 | Lieber et al. | 604/99 |
| 4,444,188 | 4/1984 | Bazell et al. | 604/97 |
| 4,464,175 | 8/1984 | Altman et al. | 604/99 |
| 4,651,738 | 3/1987 | Demer et al. | . |
| 4,723,556 | 2/1988 | Sussman | 604/97 |
| 4,776,347 | 10/1988 | Matthews | 604/99 |
| 4,981,470 | 1/1991 | Bombeck, IV | 128/780 |
| 5,135,488 | 8/1992 | Foote et al. | . |
| 5,163,906 | 11/1992 | Ahmadi | 604/101 |
| 5,171,299 | 12/1992 | Heitzmann et al. | 604/100 |

OTHER PUBLICATIONS

Abele (1980) AJR 135:901-906.
Zollikofer et al. (1985) Fortschr. Röntgenstr. 142, 5:527-530.
Demer et al. (1991) J. Am. Coll. Cardiol. 18:1259-1262.
Hjemdahl-Monsen et al. (1990) J. Am. Coll. Cardiol. 16:569.
Serruys et al. (1984) Am. J. Cardiol. 54:482-488.
Nichols et al. (1984) Circulation 69:512-522.

*Primary Examiner*—Lee S. Cohen
*Assistant Examiner*—Robert L. Nasser, Jr.
*Attorney, Agent, or Firm*—Townsend and Townsend Khourie and Crew

[57] ABSTRACT

A system includes a catheter (10) having a low pressure balloon (42) at of one end thereof, a precise, low pressure, low volume fluid infusion means (41) and a pressure sensor (43). The balloon (42) is introduced to a body lumen, such as a blood vessel, and inflated to a pressure at or just above physiologic, typically being below 200 mmhg. From the balloon volume at a particular pressure, the internal cross-sectional area and diameter of the vessel can be calculated. Additional calculations can be made at other pressures below 200 mmhg to determine compliance of the vessel.

35 Claims, 7 Drawing Sheets

APPARATUS AND METHOD FOR DETERMINING PHYSIOLOGIC CHARACTERISTICS OF BODY LUMENS

BACKGROUND OF THE INVENTION

1. Field of the Invention

The present invention relates generally to the field of medical diagnostics. More particularly, the present invention relates to the design and use of catheters for determining physiologic characteristics of body lumens, such as the diameter and wall compliance of blood vessels.

Many bodily diseases and/or abnormalities can be diagnosed by measuring the condition, i.e. size and/or compliance, of body members, one example is the vascular disease atherosclerosis, which involves the narrowing of a blood vessel such as an artery. Such narrowed regions are often referred to as lesions, stenosed regions, and the like. The narrowing of the blood vessel in turn results in the restriction, and in extreme cases, the cessation, of blood flow to the capillary system served by that particular artery. Treatment for atherosclerosis has included both surgical and non-surgical techniques. The surgical techniques involve the removal of the portion of the vessel containing the disease and replacement thereof with a vessel segment taken from another part of the body. Non-surgical techniques involve the use of an intravascular catheter. These techniques include mechanical devices which remove the occluding material in the vessel, laser devices which vaporize the occluding material, and balloon catheter devices which compress the occluding material against the vascular wall.

Heretofore, atherosclerosis has usually been diagnosed by inserting a catheter into the vessel of interest and then injecting a contrast agent into the vessel through the catheter. The blood flow will carry the contrast agent along the vessel so that the vessel can be radiographically imaged with a display device such as a fluoroscope. The radiographic image of the vessel is then reviewed in order to estimate the internal diameter of the vessel to determine if there is any abnormal narrowing of the vessel which may have occurred due to disease. If any narrowing is observed, the extent (percentage) of narrowing is estimated from the radiographic image by measuring the vessel diameter both at and immediately before the region of narrowing with a ruler, calipers or similar device. Such a measurement is typically not particularly accurate since it relies on discerning an ill-defined boundary in a single plane. Additionally, stenotic material outside of the image plane can be missed. These results in average errors of approximately 30%. Such inaccuracy hinders adequate characterization of vascular disease.

Another significant vascular condition known as "hardening of the arteries" typically occurs with aging and is characterized by the vessel wall becoming rigid, resulting in a lost capacity to expand and contract during the cardiac cycle. Normally, the vessel wall is sufficiently compliant that it expands as blood pressure rises and contracts as blood pressure falls within each cardiac cycle. It would be quite useful to accurately measure the compliance of vessel walls to determine the location and extent of non-compliant portions of the vascular system. It would be particularly useful to make such a determination prior to any interventional therapy, such as balloon angioplasty, which results in physical alteration of the atheroma and/or, blood vessel wall. Such early determinations would be of great value in selecting the mode of interventional therapy, best suited for the patient's condition.

The accurate measurement of both size and compliance of other body members, including the intestines, the urethra, and the cervix, among others, would also assist in the determination of particular conditions and/or the diagnosis of disease in those members.

Hence, there is a significant need for a system capable of accurately and directly determining in vivo the size and optionally the compliance of blood vessels, as well as other body members. Such a system should be relatively simple to use and relatively inexpensive, to accommodate a single-use strategy.

2. Description of the Background Art

U.S. Pat. No. 4,651,738, describes a method and system for monitoring the pressure-volume relationship in an angioplasty balloon during conventional angioplasty procedures. The pressure-volume relationship may be plotted on a cathode ray tube display, and the shape of the resulting curve may be used to predict the likelihood of success of the angioplasty treatment. The method relies on balloon inflation to high pressures (up to 12 atmospheres), and no suggestion is made that lumen diameter or cross-sectional area should be measured, either before or during the angioplasty treatment. The measurement of the pressure-volume relationship during angioplasty procedures to elucidate the mechanism of lesion dilation is also described in the medical literature. See, for example, Demer et al. (1991) J. Am. Coll. Cardiol. 18:1259–1262; and Hjemdahl-Monsen et al. (1990) J. Am. coll. Cardiol. 16:569–575. The use of computer-enhanced radiographic imaging techniques for determining vascular lumen diameter before and after balloon dilatation procedures is described in serruys et al. (1984) Am J. Cardiol. 54:482–488; and Nichols et al. (1984) Circulation 69:512–522.

SUMMARY OF THE INVENTION

The present invention comprises methods, systems and apparatus for determining a physiologic characteristic, such as an internal dimension or wall compliance, of a body lumen, such as a blood vessel, the intestines, the urethra, the cervix, or the like. The method relies on introducing an incompressible fluid to a balloon disposed within the body lumen. Both the static pressure and the total volume of incompressible fluid within the balloon are monitored, and the physiologic characteristic is calculated based on the measured fluid volume at one or more pressures.

Advantageously, the methods are carried out at balloon inflation pressures which are at or only slightly above the average physiologic pressure for the particular body lumen. For arteries, the balloon will usually be inflated to a pressure of no greater than 200 Mm Hg, preferably being in the range from 50 mm Hg to 150 Mm Hg, with the particular value depending at least in part on vessel location. By employing relatively low pressures which approximate physiologic, the methods of the present invention have a minimum impact on the characteristic being determined as well as on the physical structure of the lumen itself. In particular, with blood vessels, the structure of the plaque and blood vessel wall can be assessed without significant mechanical disruption (as would be the case with methods that determine wall compliance during high pressure angioplasty procedures). An optimum treatment strategy can then be selected.

Measurement of an internal dimension, such as cross-sectional area or diameter, of the body lumen is performed by measuring the total volume of an incompressible fluid within the balloon at at least one static pressure, preferably within the ranges set forth above. The internal dimension is then calculated based on the volume of fluid required to fill the balloon, where the static pressure is sufficient to cause the balloon to contact the interior wall of the lumen. In the case of a generally cylindrical balloon, the cross-sectional area is calculated simply by dividing the volume by the known balloon length.

Measurement of body lumen wall compliance requires determination of the total volume of fluid within the balloon at at least two static pressures within the ranges set forth above. The wall compliance is then calculated based on the observed difference in fluid volume at the two static pressures.

Systems according the present invention comprise a catheter body having an inflatable balloon disposed near a distal end thereof. A means for introducing a measured volume of an incompressible inflation medium is connected to the balloon through an inflation lumen which extends from the proximal end of the catheter body. A means for measuring the pressure of the inflation medium within the balloon is provided, and another means is connected to both the introducing means and the measuring means for calculating the desired physiologic characteristic based on the measured volume of the inflation medium at one or more pressures below 200 Mm Hg. The preferred inflatable balloon is generally cylindrical and has a length which depends on the characteristic being measured, usually being in the range from 3 mm to 10 mm for dimensional measurements in blood vessels. The diameter will be slightly greater than that of the lumen being measured, typically being in the range from 1 mm to 5 mm for blood vessels. The pressure measuring means comprises a pressure sensor which is preferably disposed either within the balloon or within a separate pressure measurement lumen within the catheter body.

DESCRIPTION OF THE SPECIFIC EMBODIMENTS

For the purposes of the present specification and claims, the following terms and phrases are defined as follows.

The phrase "physiologic characteristic" is intended to mean a physical or mechanical characteristic of a body lumen, particularly including internal dimensions and wall compliance. Exemplary internal dimensions include cross-sectional area, diameter, and the like. These dimensions will typically be average values determined over a preselected length of the body lumen, where the preselected length is usually defined by the length of an inflatable balloon, as described in more detail below. Wall compliance generally refers to the elasticity or resilience of the body lumen in response to an increase in internal pressurization. Wall compliance may be expressed as a percentage increase in a cross-sectional area in response to a given increase in pressure.

The phrase "body lumen" is intended to include all hollow body organs, vessels, passages, and the like, particularly including blood vessels, the intestines, the urethra, the cervix, and the like.

The phrase "static pressure" is intended to refer to the gauge pressure, i.e. pressure above ambient, within the balloon which is free from pressure transients, back pressure (dynamic pressure drop), and the like. Static pressure within the balloon is thus preferably measured by a pressure sensor element within the balloon itself or by a pressure sensor located within a separate balloon pressure measurement lumen where a static column of fluid can be maintained. It will also be possible to measure the static pressure at the inlet of the balloon inflation lumen (as described in more detail below), but any transient pressure variations, such as pressure drop during fluid infusion, must be taken into account in determining the true internal pressure of the balloon.

The phrase "measured volume" refers to the volume of incompressible inflation medium within the balloon. Usually, the volume will be measured using a calibrated positive displacement mechanism for introducing the incompressible inflation medium to the balloon, usually a calibrated syringe which may be driven by a stepper motor or a servo-controlled motor. In the case of internal dimension measurements, it will be necessary to determine the absolute volume of fluid within the balloon, excluding volumes within the inflation lumen, pressure measurement lumen (if employed), fluid introducing means, and the like. In the case of wall compliance measurements, it will usually be necessary to measure only differential volume between two different values of static pressure.

The phrase "incompressible fluid" is intended to include a variety of liquids of the type normally employed for the inflation of intravascular balloons, e.g., angioplasty balloons. Exemplary incompressible fluids include sterile water, saline, contrast media (typically diluted with water), and the like.

Figure 1:
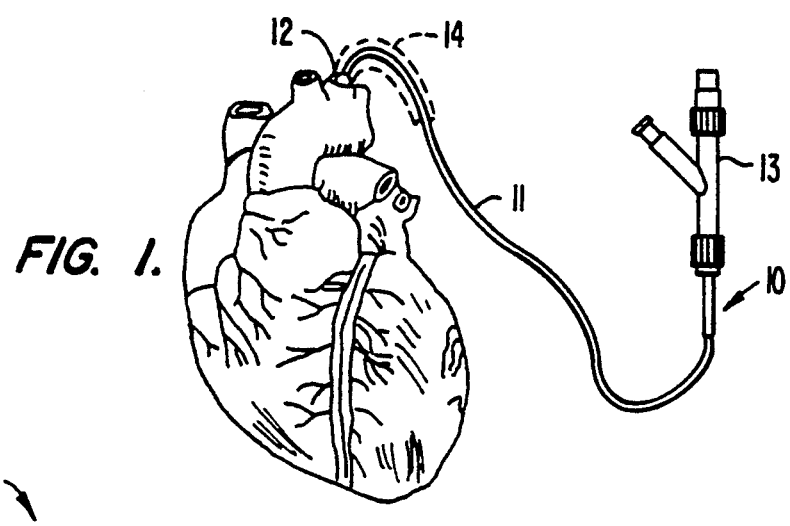
FIG. 1 is a simplified schematic diagram showing a catheter useful in the present invention in place for one specific application in a section of an artery adjacent the heart.

Referring generally to FIG. 1, an apparatus 10 constructed in accordance with the principles of the present invention includes a catheter body having a balloon portion 12 near its distal end and a housing or manifold 13 at its proximal end. The balloon 12 is illustrated in an artery 14 (shown in broken line) adjacent the heart 16.

Generally, in order to determine the condition of a vessel, such as the artery 14 in FIG. 1, using the present invention, an unconstrained (such as in air) balloon catheter is inflated and infused fluid volume measurements are made for successive selected balloon fluid pressures, typically in the range of 0-200 millimeters of mercury (mm Hg). The balloon is then deflated and inserted into the vessel or other body member of interest, and measurements of infused fluid volume are made again for the same successive selected balloon fluid pressures. The data from these two sets of measurements are then used to calculate vessel internal dimensions, such as cross-sectional area or diameter, at each selected balloon fluid pressure.

It will be appreciated that it will not always be necessary to perform the initial inflation of the unconstrained balloon. By providing catheters having known and predictable inflation characteristics, it will be possible to "precalibrate" the methods and systems of the present invention. That is, the physiologic characteristic calculations may be made based on known expansion characteristics of the balloon and other system components so that the need to individually calibrate each balloon is avoided.

The balloon catheter 10 can be similar to that which is commercially available and conventionally used for the intravascular angioplasty technique, provided that the balloon portion of the catheter is shortened and the balloon material selected to facilitate balloon operation at low fluid pressures. Conventional balloons used for angioplasty are relatively long while the balloon of the present invention will vary between a few millimeters to several centimeters (typically having a length from 3-10 mm for dimensional measurements in blood vessels) and hence can be more location specific along the vessel being measured. The balloon diameter will be slightly greater than the lumen being measured (typically being from 1 mm to 5 mm for dimensional and/or compliance measurements in blood vessels). Conventional angioplasty balloons are designed to withstand 6-15 atmospheres of pressure (one atmosphere equaling 760 Mm Hg). The angioplasty balloon material is necessarily fairly thick (typically approximately 3 mils) to prevent rupture. However, a thick wall balloon does not readily conform to vessel internal geometry. Additionally, thick wall balloons are characterized by irregular balloon fluid pressure during inflation, due to the unfolding of the stiff balloon material.

The balloon portion of the present invention is designed to operate at much lower pressures, typically within the range of 0-200 mm Hg, since this is the range of pressures normally present in a blood vessel or other body member. A low pressure balloon may be made of thinner material (1 mil or less), resulting in the balloon having improved conformance to vessel walls and reducing balloon unfolding pressure artifacts during inflation. Thinner material allows the balloon to be folded in such a manner to further reduce inflation artifacts. A low pressure balloon thus will likely provide more accurate, reliable results in the physiologic pressure range.

In the basic operation of the balloon catheter used in the system of the present invention for measurement of vessel dimensions, as with other balloon catheters, the tip of the catheter is inserted, for example, into a vessel at a convenient point, with the catheter then being manipulated by a trained operator through the vascular system, until the balloon portion thereof reaches the point of interest in the vascular system.

Figure 4:
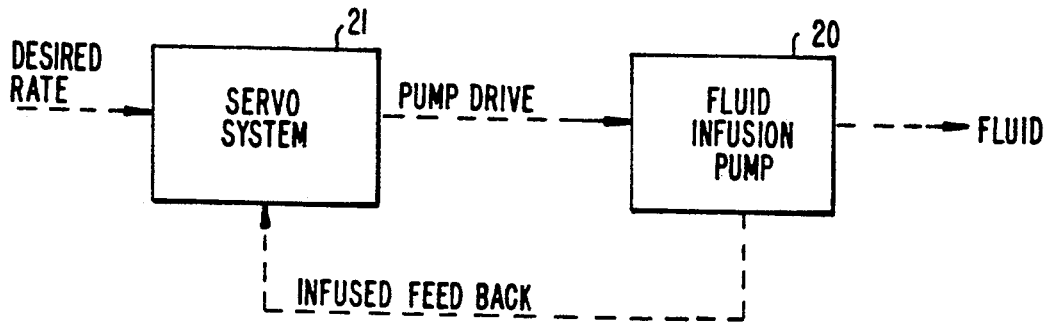
FIG. 4 is a block diagram of the control portion of the system of the present invention.

Referring to FIG. 4, the infusion of fluid into the catheter balloon may be accomplished by a positive displacement device, such as a fluid-infusion pump 20 which is driven under the control of a servo system 21 which is responsive to a predetermined fluid infusion rate schedule and a measured (feedback) value of actual infused fluid volume. The rate of infusion may be varied during the infusion process according to a predetermined pattern or schedule. Such a schedule, for instance, may be important because of inertial forces associated with starting and stopping the fluid infusion pump. The use of rate schedules permits the cancellation of viscous flow effects associated with fluid flow in the catheter. Alternatively, the pump 20 may be driven by a stepper motor with no need to provide feedback control.

Figure 5:
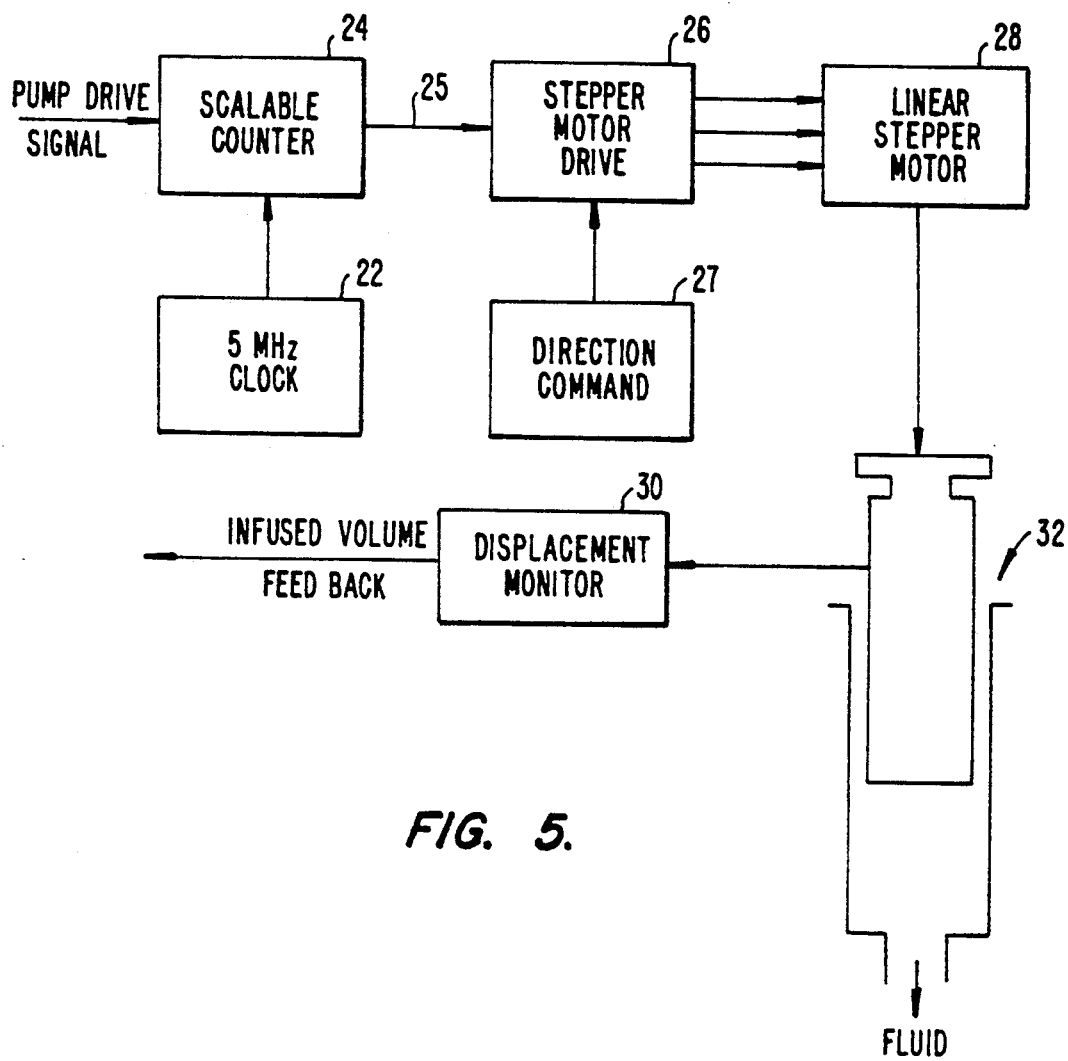
FIG. 5 is a detailed block diagram of the fluid infusion pump portion of the system of the present invention.

Referring specifically to FIG. 5, a fluid infusion pump 20 in the form of a calibrated syringe is driven by a linear stepper motor 30 by a control system comprising a 5 megahertz clock signal from a source 22 thereof applied to a counter 24 which is set to produce drive pulses on output line 25 to a stepper motor drive 26, which is also responsive to a direction command from circuit 27. The stepper motor drive 26 controls the stepper motor 28 which in turn controls a gas-tight syringe 32. The syringe infuses the fluid into the catheter and eventually into the balloon portion located at the tip thereof.

In the embodiment shown, the infusion system is designed to produce a precise fluid infusion of 10-200 microliters ($\mu$l) of fluid at a selected rate of 10-50 $\mu$l/sec. The fluid in the syringe should be sterile, relatively bubble-free, and substantially incompressible. The action of syringe 32 may optionally be detected by a displacement monitor 30 which confirms the actual infused volume. It should be understood, however, that both the fluid infusion rate schedule and the total infused volume can be varied depending upon the application. Also, while the above-described system produces satisfactory results in the system of the present application, it should be understood that other arrangements, and/or other components, could be used for fluid infusion. For example, in some applications, the feedback signal from pump 20 may not be necessary.

Figure 2A:
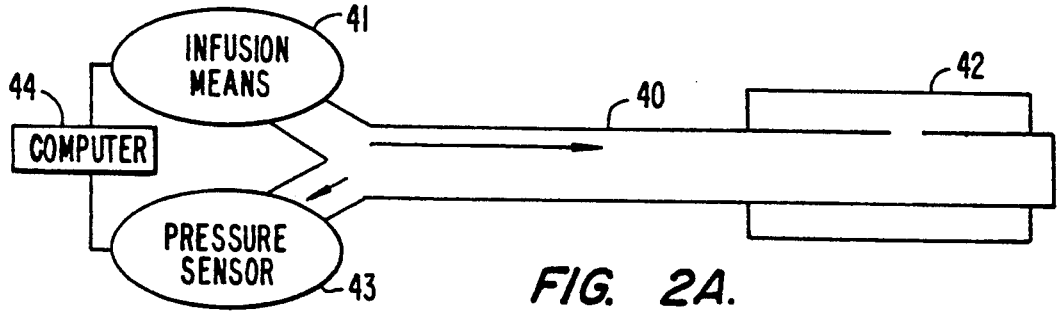
FIG. 2A is a simplified illustration of a catheter system constructed in accordance with the principles of the present invention.
Figure 2B:
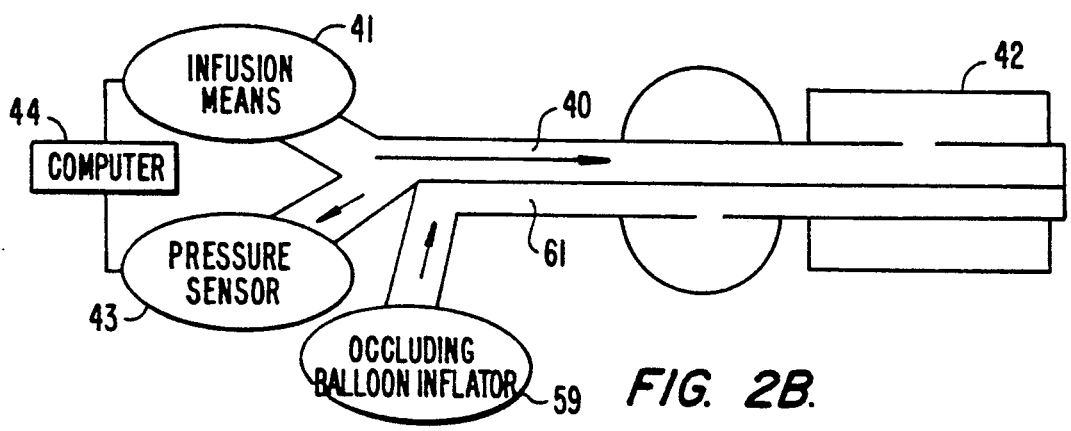
FIG. 2B is a simplified illustration of a catheter system of the present invention which employs an occluding balloon.
Figure 2C:
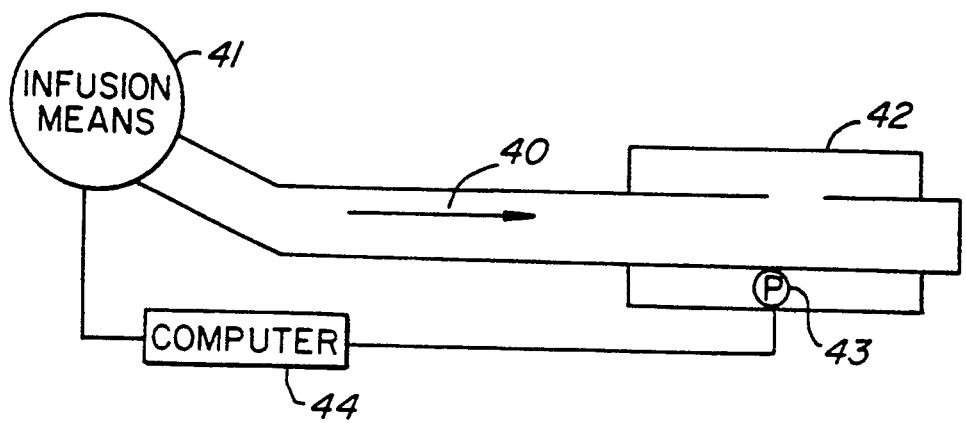
FIG. 2C is a simplified illustration of a catheter system of the present invention which has a pressure transducer within the balloon.

Referring now to FIG. 2A, relative to the operation of the complete system, a single lumen catheter 38 is shown for illustration. In this embodiment, fluid is directed through the single lumen opening 40 by an infusion system 41, such as discussed above, to the balloon 42, resulting in the balloon 42 being filled. In the embodiment of FIG. 2A, the same lumen opening 40 through which fluid is infused into the balloon 42 is used for measurement of the fluid pressure in the balloon, such as by pressure sensor 43 in FIG. 2A. Both the fluid infusion system 41 and the pressure sensor 43 are connected to a computer 44. In the embodiment shown, pressure sensor 43 is a standard semiconductor strain gauge pressure transducer, having a pressure rating of 50-1000 mm Hg, and a resolution of 0.5 Mm Hg. Alternatively, a microminiature pressure transducer could be positioned in the lumen opening 40 near the balloon 42 or perhaps and preferably within the balloon itself in a particular application. A catheter system having a microminiature pressure transducer 43 located within the balloon is depicted in FIG. 2C. Semiconductor strain gauge pressure transducers or fiber optic pressure sensors are available in sufficiently small sizes for such alternative embodiments.

It is important for accurate results that the pressure in the balloon itself be determined. For instance, the balloon pressure is generally not identical to the pressure at the proximal end 45 of the catheter. The pressure measurements at the proximal end of the catheter are influenced by the back pressure caused by the viscous forward flow of fluid toward the balloon. In addition, the pressure transducer, when it is relatively remote from the balloon, will produce a pressure measurement which in fact is influenced by several variables, in addition to balloon fluid pressure, including catheter wall compliance, catheter wall movement, external catheter wall pressure, and the fluid infusion rate.

Figure 3:
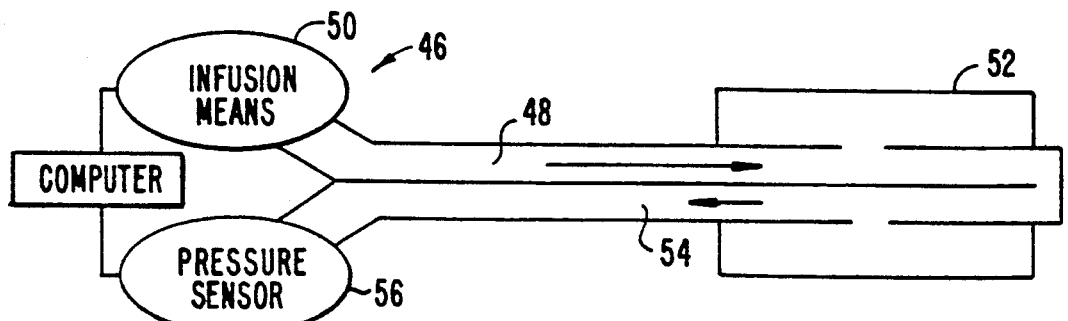
FIG. 3 is a simplified illustration of a catheter system of the present invention which employs a pressure sensor disposed in a separate lumen.

In order to solve such problems, the embodiment shown in FIG. 3 can be used. In this embodiment, a double lumen catheter 46 is used, in which one lumen 48 is used for fluid infusion from a fluid infusion system 50 to balloon 52, while a second fluid-filled lumen 54 is for fluid pressure measurement in the balloon 52, by pressure sensor 56. Both the infusion system 50 and pressure sensor 56 are connected to a computer 57. There is essentially no net fluid flow in lumen 54 during a given pressure measurement. The fluid infusion and the fluid pressure measurements are separated completely. Typically, this improves the accuracy of the balloon fluid pressure measurements, although, in some cases, such increased accuracy is not necessary.

The balloon 42/52 in the embodiments of FIG. 2A or 3 is designed to readily withstand a pressure of up to at least 200 mm Hg without significant stretching, yet also be flexible enough to conform to irregularities in the arterial walls, and unfold and open without significant resistance. The typical range of human arterial blood pressure is 70-120 mm Hg, with 100 mm Hg being a mean arterial blood pressure at the heart level. The low pressure balloon of the present invention is designed to operate over this physiologic pressure range normally experienced by the artery. In its fully inflated state, the balloon will form a cylinder, the length of which will typically be iv the range of 3-10 mm. Since the measurement of artery condition, such as cross-sectional area, is averaged over the entire length of the balloon, a shorter balloon length will allow measurement of cross-sectional area over a short distance, approximating a point measurement. This is important for accurate mapping of disease along the length of the artery, particularly since such disease may be unevenly distributed along the artery. It should also be understood that the balloon can be made in several different sizes (outside diameter) so that measurements of small, medium, and relatively large arteries (or veins or other tubular body members) can be more readily accommodated. Normal requirements of stiffness/flexibility apply to the catheter body itself for intravascular maneuvering.

Figure 3A:
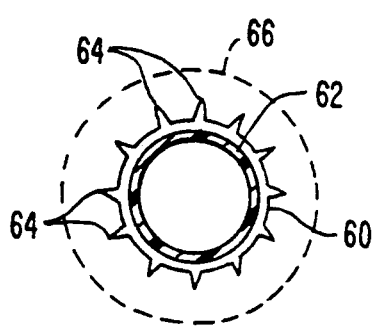
FIG. 3A is a cross-sectional view of an exemplary balloon profile.
Figure 3B:
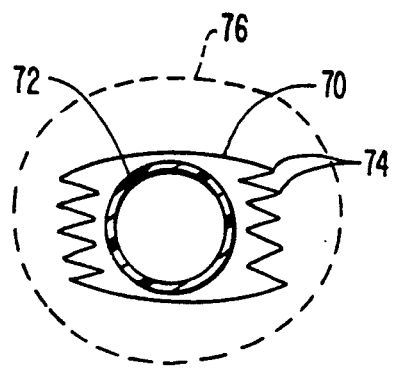
FIG. 3B is a cross-sectional view of a second exemplary balloon profile.

Exemplary balloon profiles which are useful in the catheter devices of the present invention are illustrated in FIGS. 3A and 3B. In FIG. 3A, a balloon element 60 is disposed coaxially over catheter body 62. The balloon element 60 is folded in a "flower petal" pattern with a plurality of discrete folds 64 which extend axially along the entire length of balloon 60. The balloon 60 may be inflated to the dimensions shown in broken line 66 by internal pressurization, as described previously. It is believed that the use of the segmented folding pattern provides for a smooth and uniform expansion which is substantially free from induced pressure transients and other unfolding artifacts which could adversely affect monitoring of the internal balloon pressurization.

The pattern of FIG. 3B is similar to that of FIG. 3A, with a balloon 70 disposed coaxially about catheter body 72. The balloon 70 includes a plurality of axial folds 74 which are stacked in an "accordion" pattern. Upon internal pressurization, the balloon 70 expands to the pattern shown in broken line 76.

It should be further understood that an additional, proximal balloon can be added to the catheter, as well as a separate inflation lumen therefor, to occlude blood flow in the vessel segment while measurements are made by a distal balloon such as described above. An example of such an arrangement is shown in FIG. 2B. FIG. 2B is a variation of FIG. 2, with the addition of an occluding balloon 58, an occluding balloon inflator 59 and an occluding balloon lumen 61. The locations of the respective balloons can be reversed, depending on blood flow direction.

In a variation of the fluid infusion system of FIGS. 2 and 3, the catheter could be a closed system, with a sterile fluid being moved within the catheter by a bellows arrangement used as the infusion system.

Figure 6:
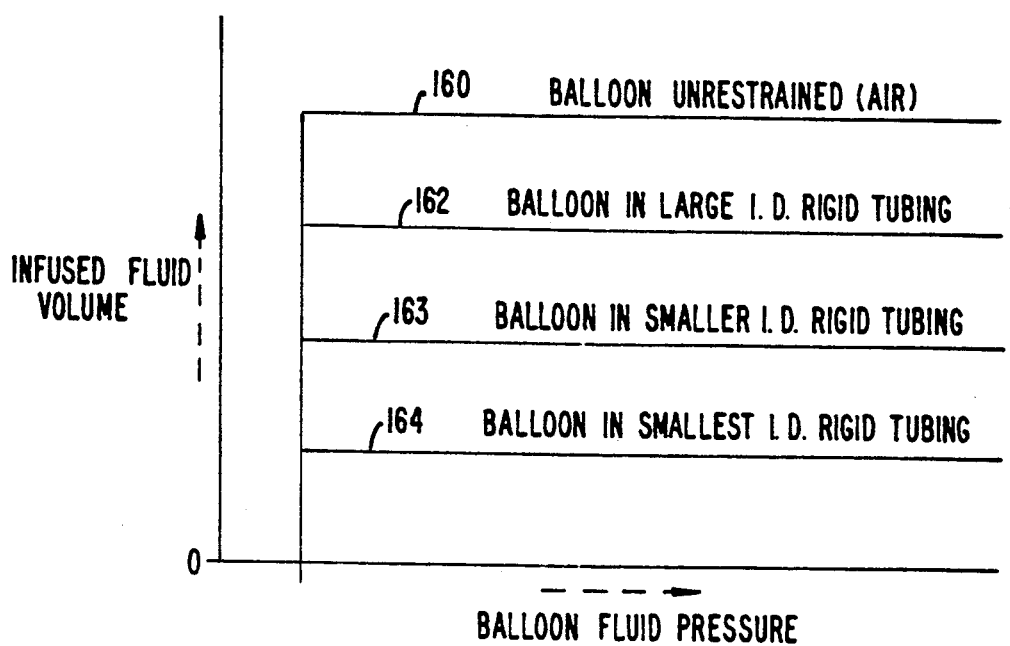
FIG. 6 is a set of ideal curves of fluid volume infusion against pressure for the system of the present invention, when the balloon portion of the catheter is unrestrained and then inside various sizes of rigid tubing.
Figure 7:
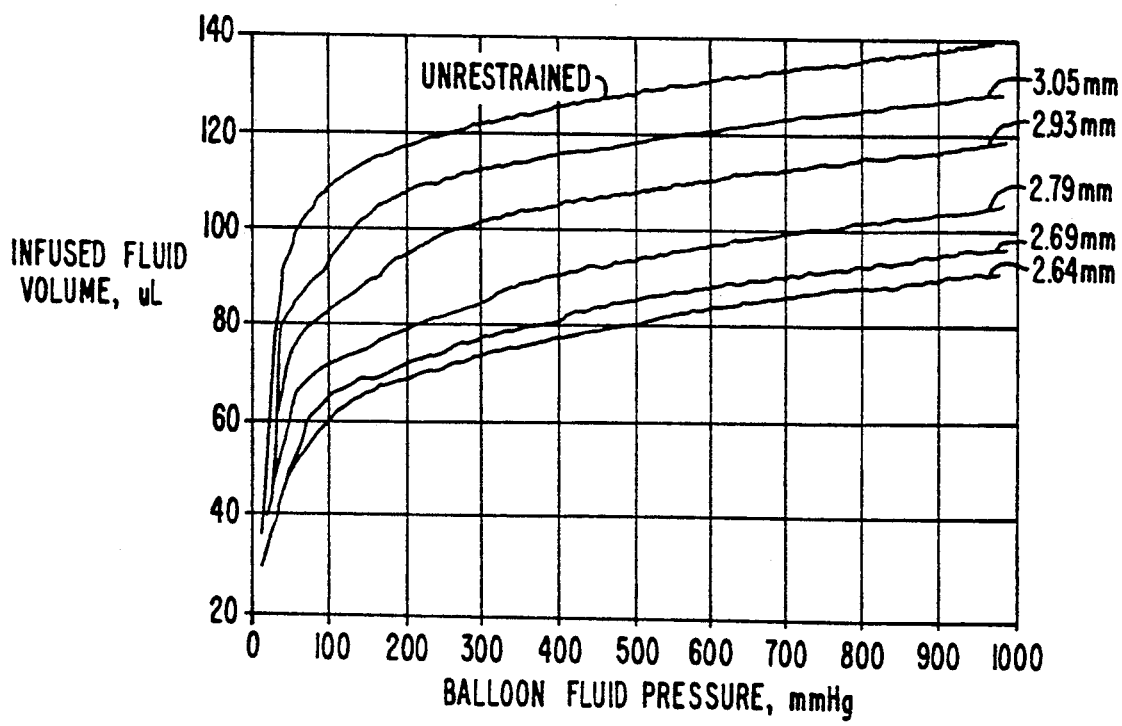
FIG. 7 is a set of actual recorded curves of fluid volume infusion against pressure for the system of the present invention, when the balloon portion of the catheter is inside various sizes of rigid tubing.
Figure 8:
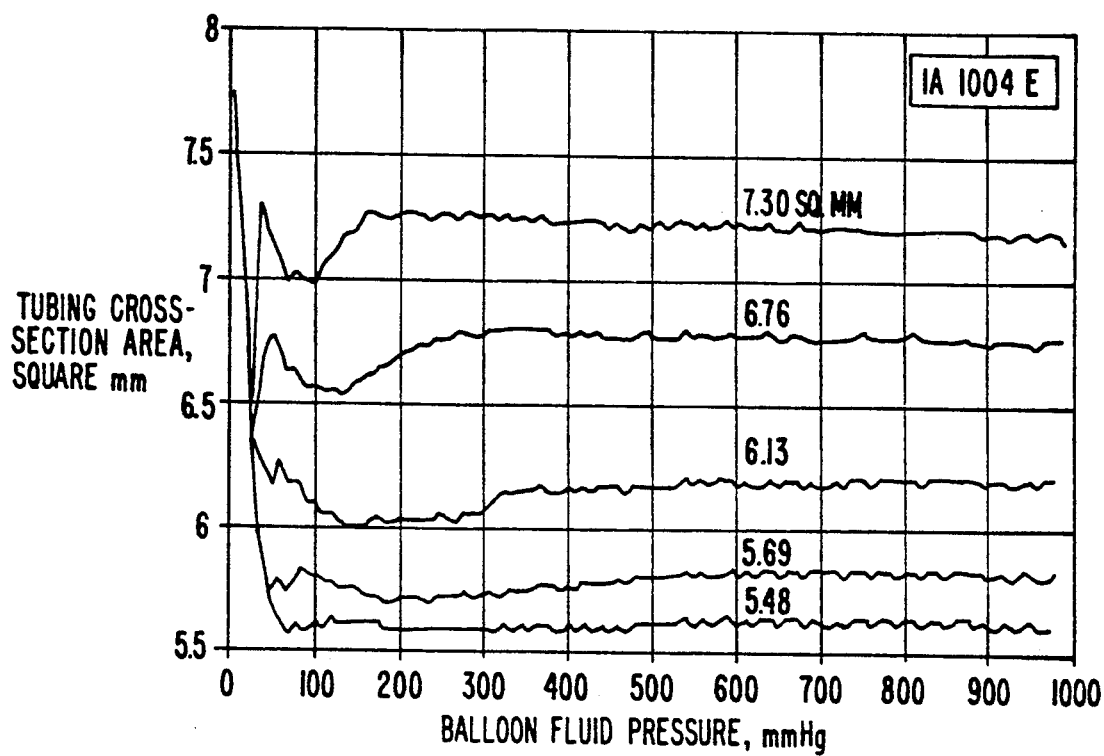
FIG. 8 is a set of calculated curves of tubing cross-sectional area against pressure for the system of the present invention, when the balloon portion of the catheter is unrestrained and then inside various sizes of rigid tubing.

FIGS. 6, 7 and 8 illustrate the theoretical analysis performed by the inventors which led to the present invention, specifically a system for accurately determining size and compliance information from pressure-infused volume data using a balloon catheter.

During fluid infusion of an ideal balloon catheter (made of non-compliant materials) which is unrestrained, balloon fluid pressure will typically remain near zero as fluid infusion is first initiated and then continued until the balloon is completely filled, at which point the balloon fluid pressure will increase substantially. This ideal pressure-volume response of an unrestrained balloon is shown as curve 160 in FIG. 6 and can be characterized mathematically as follows: $V_a(P)$ = volume displaced by balloon—volume of balloon wall + volume of catheter.

$$V_a(P) = \frac{\pi d_0^2 L}{4} - \pi d_0 L t + V_c \quad \text{(Equation \#1)}$$

where $V_a(P)$ = the infused fluid volume of a catheter with an unrestrained balloon at a selected pressure (P) which is greater than zero, $d_o$ = the outside diameter of the inflated balloon at the selected pressure, L = balloon length (inflated), t = balloon wall thickness and $V_c$ = the volume of the catheter lumen at the selected pressure.

FIG. 6 also shows the pressure-volume response curves for the ideal balloon catheter of curve 160 positioned in a number of different rigid tubes, all having a smaller inside diameter than the outside diameter of the fully inflated ideal balloon. In such a situation, the balloon will fill with fluid while the pressure remains near zero until the balloon contacts the internal surface of the rigid tubing, at which point the balloon fluid pressure will increase substantially. This is shown as curves 162-164 in FIG. 6.

This situation can be characterized mathematically as follows: $V_t(P)$=volume of the balloon when it contacts the inner surface of the rigid tubing—volume of balloon wall+volume of catheter lumen.

$$V_t(P) = \frac{\pi d^2 L}{4} - \pi d_0 L t + V_c \quad \text{(Equation \#2)}$$

where $V_t(P)$=the infused fluid volume of a catheter with its balloon placed within a rigid tube having a smaller inside diameter than the outside diameter of the fully inflated balloon at a selected pressure (P) which is greater than zero and d=internal diameter of the rigid tubing.

Reviewing the equations 1 and 2 above, it can be seen by virtue of appropriate substitution that:

$$V_t(P) - \frac{\pi d^2 L}{4} = V_a(P) - \frac{\pi d_0^2 L}{4}$$

hence:

$$V_t(P) - V_a(P) = \frac{\pi d^2 L}{4} - \frac{\pi d_0^2 L}{4}$$

since $$\frac{\pi d^2}{4} = \text{cross-sectional area } (A),$$

the cross-sectional area of the tubing can be calculated as follows:

$$A = \frac{[V_t(P) - V_a(P)]}{L} + \frac{\pi d_0^2}{4} \quad \text{(Equation \#3)}$$

$$A = \frac{\pi d_0^2}{4} - \frac{[V_a(P) - V_t(P)]}{L} \quad \text{(Equation \#4)}$$

From the above, it is clear that the interior cross-sectional area of the tubing can be calculated if the length of the balloon is known, and if $V_a$ and $V_t$ are known for a particular pressure P. Since the length of the balloon and the outside diameter of the inflated balloon are known characteristics of the balloon, and since $V_t$ and $V_a$ can be measured at one or more discrete pressures with the system of the present invention, the system of the present invention can hence be used to determine the interior cross-sectional area of the tubing at the discrete pressures.

The value of the above analysis is that equation 4 for cross-sectional area is shown to remain valid not only for ideal balloon catheters but also for real balloon catheters, which may include partially compliant materials used in real (compliant) blood vessels and/or other body members in animals and humans. FIG. 7 shows experimental results in which a commercially available angioplasty balloon catheter was infused with fluid, first in ambient pressure air (unrestrained) and then in rigid tubing of different internal diameters. The pressure-volume response curves of FIG. 7 are not flat,, like those for an ideal catheter, but rather show a gradual continual increase in infused fluid volume as pressure increases, beyond the point of nominal filling of the balloon. This is due to many factors, including the compliance of the catheter wall and fluid frictional forces, among others. FIG. 7 does demonstrate, however, that the pressure-volume curves of an angioplasty catheter in different size rigid wall tubings have the same basic shape, and that they are displaced from the pressure volume curve of the same catheter in air (unrestrained).

Applying equation 4 to the data of FIG. 7, a new set of curves is produced, as shown in FIG. 8. Initially, it should be understood that the curves of FIG. 7 were obtained with a balloon catheter designed for operation at high pressures (6–15 atmospheres). Such balloons have thicker walls than required for the present invention. They have a significant resistance to opening, and hence, the curves of FIG. 8 include balloon unfolding artifact in the low pressure range (0–500 mm Hg). A balloon catheter specifically designed for use at low pressure, as discussed above, will produce accurate measurements in the range of interest (50–200 Mm Hg). Importantly, equation 4 gives a reliable cross-sectional area determination independent of the compliance characteristics of the balloon catheter. The results shown in FIG. 8 correlate very closely with the actual internal diameters of the various rigid wall tubes.

Figure 9:
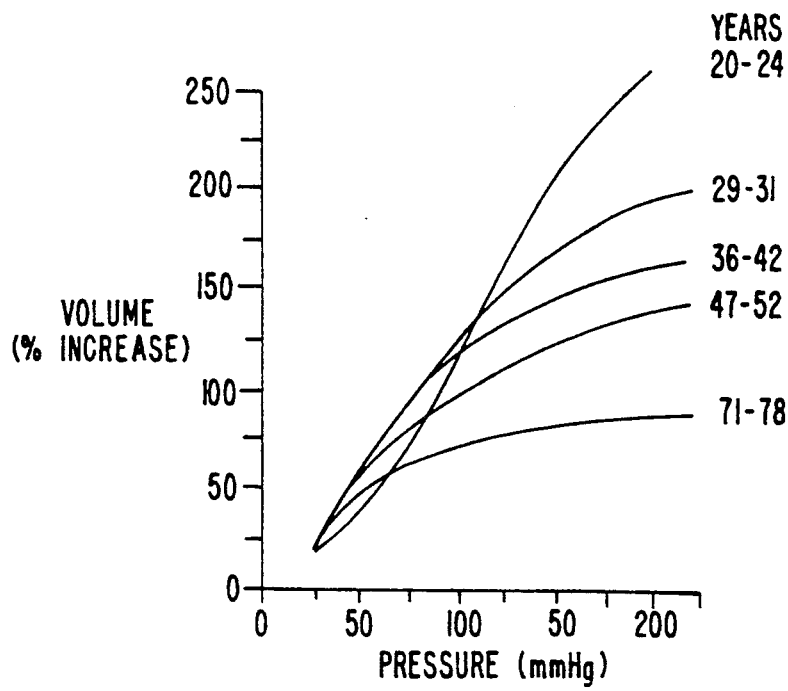
FIG. 9 is a set of curves showing compliance of human aortas at various ages.

Actual blood vessels, of course, are typically compliant to some extent. This is shown by the pressure-volume curves of FIG. 9 which were obtained in vitro from cadaver vessels, using other methods, disclosed in *Circulation Physiology*, J. J. Smith and J. P. Kampine, 1980. If such vessels were investigated in vivo using the system of the present invention, the cross-sectional area of the vessel would increase slightly following the infusion of additional fluid beyond that necessary to just produce contact between the balloon and the interior surface of a vessel. The change in cross-sectional area with an increase in pressure is a measure of vessel compliance. The present invention can thus not only produce an accurate result for cross-sectional area, but also provide direct, n vivo information on vessel compliance as well.

In general operation of the system of the present invention, infused fluid volume is first measured at one or more preselected pressure values for the particular balloon catheter being used when the balloon is unrestrained. A typical range of pressure values is 0–200 mm Hg. The deflated balloon catheter is then positioned in the vessel or other body member such as the intestine or the urethra and the balloon manipulated to the point of interest. The infused fluid volume is then measured at the same preselected pressure values, again for the range of 0–200 mm Hg. In each case, fluid is infused into the balloon in accordance with a predetermined rate schedule involving known fluid infusion rate amounts at specific pressure intervals. The vessel cross-sectional area is calculated using equation 4, either after each pressure-volume measurement or after all the pressure-volume measurements have been made. The cross-sectional area determination at a pressure of approximately 100 mm Hg, which is the typical pressure in the vessel, will provide the physiologically useful cross-sectional area information concerning the vessel, while a plurality of area determinations, at two or more pressures, will provide information on the compliance of the vessel.

Figure 10:
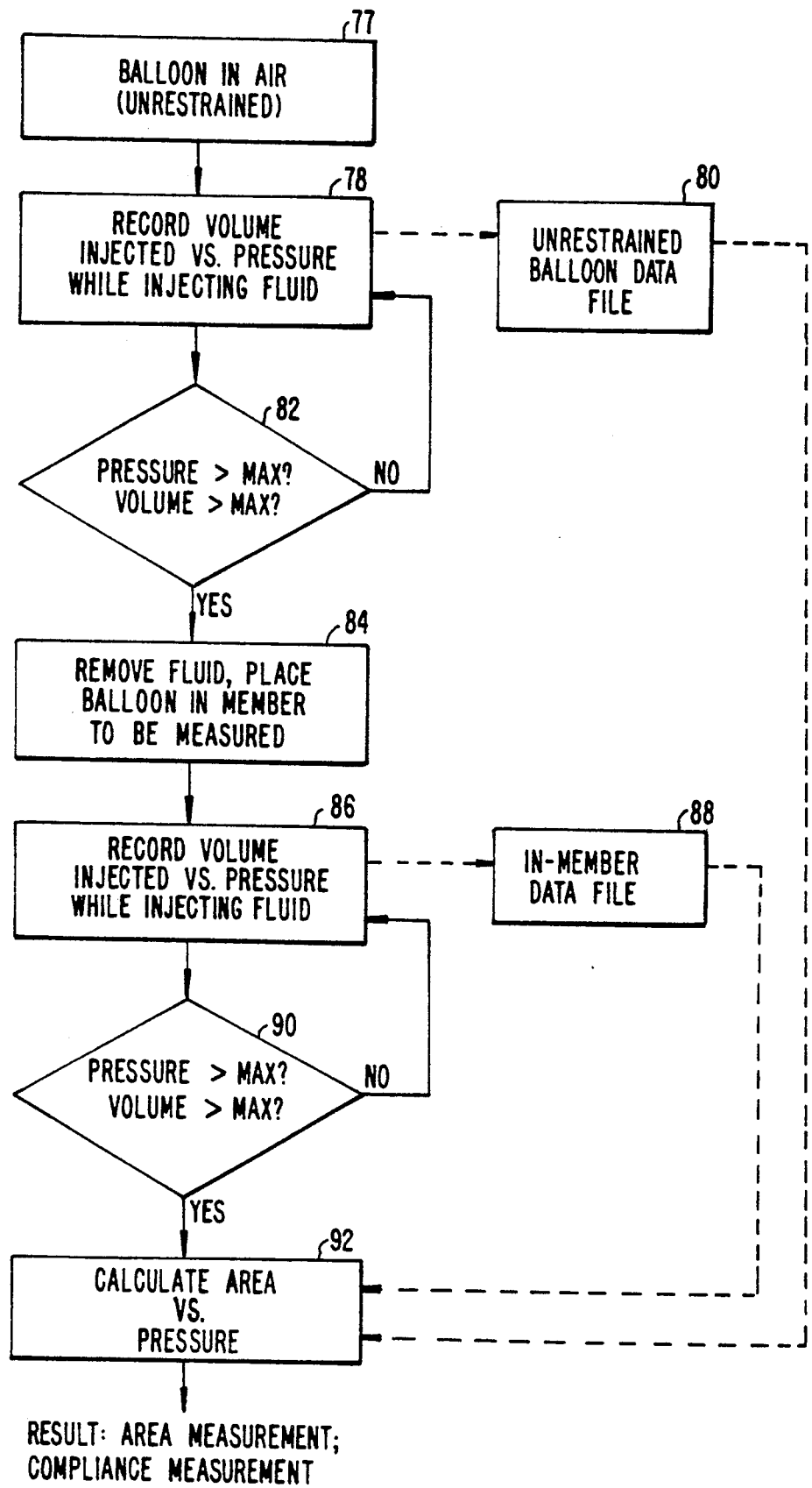
FIG. 10 is a simplified flow diagram for the software of the present invention.

In more detail with respect to the operation of the present invention, FIG. 10 is a flow chart showing the software which controls the operation of the present invention, in combination with successive process steps. First, a balloon catheter is positioned such that the balloon is unrestrained, such as in air, shown at block 77. This could be done, for instance, by laying the catheter on a table top and then inflating it. Since the polymer materials of the balloon and catheter have mechanical properties that are generally temperature dependent, it may be helpful to perform the steps of inflation at body temperature, i.e. 37° C. The volume of infused fluid, which could be a liquid such as a normal saline solution, is measured and recorded at preselected values of pressure within the specified pressure range, as the balloon is being filled, as shown at block 78. The temperature of the infused fluid should preferably, but not necessarily, be at body temperature. This data is stored in an unrestrained balloon data file, as shown by block 80. When a predetermined maximum balloon fluid pressure or maximum infused fluid volume is reached, the measuring, recording and storing process is terminated and the fluid is removed from the balloon, as shown in blocks 82 and 84.

The balloon catheter is then placed in a vessel or other body member and then manipulated so that the balloon portion is at the particular point of interest,, as shown in block 84. The pressure/volume measurements are repeated, as shown in block 86, and the data is stored in an in-member data file, as shown in block 88. When the maximum balloon fluid pressure or infused fluid volume level is reached, the fluid is removed from the balloon, as shown in block 90. Generally, it is anticipated that a single pressure-volume curve can be obtained in approximately 1-3 seconds. If it is desired to remove certain artifacts from the recorded pressure-volume data, such as that caused by blood pressure, the pressure-volume data can be recorded only during the low pressure (diastolic) phase of the cardiac cycle or averaged over a number of cycles.

The cross-sectional area of the vessel or other body member is then calculated at a number of balloon fluid pressures using equation 4 above, as shown by block 92. The effective inside diameter $d_e$ of the member can then be calculated from the various area determinations by use of the formula $d_e \sqrt{4A/\pi}$. As indicated above, the most physiologically useful area determination is one made at the mean vessel pressure, which is typically about 100 Mm Hg for arteries. Resulting area information is anticipated to be accurate to ±2%, with a repeatability error of less than ±2%, providing significant improvements over existing dimension measuring techniques.

The area and diameter calculations taken as a whole will show increases in area and diameter with increases in pressure. A plot of this information will show the compliance of the vessel, similar to the data shown in FIG. 9. This information is quite significant and important in determining the condition of vessels, as indicated above, but has not been possible prior to applicants' invention.

When the cross-sectional area or diameter of the vessel is determined using equation 4, it should be understood that the balloon fluid pressure P at which the determinations are made is not exactly the pressure at the vessel wall itself. It is important, particularly with respect to compliance determinations, that the pressure in fact be the vessel wall pressure. Corrections can be made, if necessary, as follows.

For the two-lumen catheter of FIG. 3, the measured pressure is very close to the actual balloon fluid pressure, because there is essentially no net fluid flow in lumen 54. The actual pressure within the vessel is slightly less than the balloon pressure, because the balloon wall has a finite thickness and the surface area inside of the balloon is hence less than the surface area of the outside of the balloon. The actual pressure within the vessel, i.e. the pressure at the vessel wall, referred to as $P_i$, is calculated as follows:

$$P_i = P\left(\frac{d_e - 2t}{d_e}\right)^2 \qquad \text{(Equation \#5)}$$

where $d_c$ is the inside diameter of the vessel and t is the thickness of the balloon wall. Thus the cross-sectional area and diameter data for the catheter of FIG. 3 is for a given balloon pressure P, corresponding to a vessel pressure $P_i$. A correction which can be made, if desired, is to subtract the small amount of initial pressure, i.e. a threshold pressure, which is present prior to the rise in fluid volume (FIG. 7).

For the single lumen catheter of FIG. 2, a further pressure correction is necessary. Since the pressure sensor 43 is connected to the proximal end of the catheter lumen, the pressure which is measured during fluid infusion is greater than the balloon pressure. The pressure difference is that required to force the viscous fluid from the proximal end of the catheter to the balloon. This pressure is essentially that measured by the sensor during the period of fluid infusion prior to the balloon being completely filled. At a fixed fluid infusion rate, the pressure difference will be constant. This pressure difference is subtracted from the measured pressure, yielding the actual balloon pressure. Applying the pressure correction of equation 5 above will then yield the vessel pressure.

Hence, an accurate and fast apparatus and method has been described which provides size and compliance information for blood vessels. Further, the apparatus can be used to obtain similar information for other body members having an opening therein (some of which are tube-like), such as the intestines, the urethra, the cervix, etc. This information is particularly useful in the diagnosis of certain diseases affecting vessels and such body members. The accuracy of the apparatus and method exceeds significantly that of existing methods relative to size determination. The apparatus and method further provide compliance information which heretofore has not been available.

Although a preferred embodiment of the invention has been disclosed herein for illustration, it should be understood that various changes, modifications, and substitutions may be incorporated in such embodiment without departing from the spirit of the invention which is defined by the claims which follow:

What is claimed is:

1. A method for determining a physiologic characteristic of a body lumen, said method comprising:
   introducing an incompressible fluid to a balloon disposed within the body lumen;
   measuring static pressure within the balloon;
   measuring total volume of fluid within the balloon at at least one static pressure below 200 mm Hg; and calculating the physiologic characteristic based on the measured volume at said at least one measured pressure.

2. A method as in claim 1 wherein the physiologic characteristic is an internal dimension.

3. A method as in claim 2, wherein the internal dimension includes a cross-sectional area.

4. A method as in claim 2, wherein the internal dimension includes an internal diameter.

5. A method as in claim 1, wherein the physiologic characteristic is lumen compliance and the calculating step comprises calculating the lumen compliance based on a difference in the measured volume of inflation medium between a first measured pressure and a second measured pressure.

6. A method as in claim 1, wherein the step of introducing incompressible fluid comprises introducing incompressible fluid by positive displacement and the volume measuring step comprises measuring the volume based on the amount introduced.

7. A method as in claim 1, wherein the body lumen is selected from the group consisting of blood vessels, the intestines, the urethra, and the cervix.

8. A method as in claim 1, wherein the step of introducing incompressible fluid comprises introducing the fluid at a substantially constant rate in the range from 10 to 1000 µl/sec.

9. A method as in claim 1, wherein the step of introducing incompressible fluid comprises introducing the fluid at a variable rate in the range from 10 to 1000 µl/sec.

10. A method as in claim 1, wherein said at least one static pressure is between 70 and 120 mm Hg.

11. A method as in claim 1, further including the steps of stopping and then reversing the introduction of fluid into the balloon at preselected values of fluid pressure and volume.

12. A method as in claim 11, wherein the preselected fluid pressure is in the range from 0 to 200 mm Hg.

13. A method as in claim 1, including the steps of determining fluid volume for a plurality of fluid pressures below 200 mm Hg, when the balloon is unconstrained and also when the balloon is within the body lumen.

14. A method as in claim 12, wherein the incompressible fluid is introduced by positive displacement and the volume is measured based on the amount displaced.

15. A method as in claim 1, wherein the balloon is generally cylindrical and internal dimension is calculated by dividing the measured volume by a known balloon length.

16. A method as in claim 2, wherein the body lumen is selected from the group consisting of blood vessels, the intestines, the urethra, and the cervix.

17. A method for determining wall compliance of a body lumen, said method comprising:
  introducing an incompressible fluid to a balloon disposed within the body lumen;
  measuring the static pressure within the balloon;
  measuring the total volume of fluid within the balloon at at least two static pressures below 200 mm Hg; and
  calculating the wall compliance based on an observed difference in the fluid volume between a first measured pressure and a second measured pressure.

18. A method as in claim 17, wherein the step of introducing incompressible fluid comprises introducing said fluid by positive displacement and the volume is measured based on the amount displaced.

19. A method as in claim 17, wherein the step of calculating the wall compliance comprises calculating wall compliance as a percentage increase between a first measured volume at a first pressure and a second measured volume at a second higher pressure.

20. A method as in claim 17, wherein the body lumen is selected from the group consisting of blood vessels, the intestines, the urethra, and the cervix.

21. A method for calculating cross-sectional area at a location within a body lumen, said method comprising:
  inflating a balloon to a preselected pressure while the balloon is unconstrained;
  determining the internal volume of the unconstrained balloon at the preselected inflation pressure;
  introducing the balloon while uninflated to the location within the body lumen;
  inflating the balloon to the preselected pressure at the location;
  determining the internal volume of the balloon while inflated at the location; and
  calculating the cross-sectional area at the location based on the difference between the unconstrained volume and the volume at the location.

22. A method as in claim 21, wherein the preselected pressure is below 200 mm Hg.

23. A method as in claim 21, further comprising calculating cross-sectional area at a plurality of different preselected pressures, whereby compliance of the body lumen may be determined.

24. A system for measuring a physiologic characteristic of a body lumen, said system comprising:
  a catheter body having a proximal end, a distal end, and an inflation lumen extending from the proximal end to near the distal end;
  an inflatable balloon disposed near the distal end of the catheter body and being connected to the inflation lumen;
  means for introducing a measured volume of inflation medium through a proximal end of the inflation lumen to inflate the inflatable balloon to a pressure of up to 200 mm Hg;
  means for measuring the pressure of the inflation medium within the balloon; and
  means for calculating the physiologic characteristic based on the value of the measured volume of inflation medium at one or more pressures below 200 mm Hg.

25. A system as in claim 24, wherein the inflatable balloon when inflated is generally cylindrical and has a length in the range from 3 Mm to 10 Mm and a diameter in the range from 1 to 5 mm.

26. A system as in claim 24, wherein the means for introducing a measured volume of inflation medium comprises a syringe.

27. A system as in claim 24, wherein the pressure measuring means comprises a pressure sensor disposed within the balloon.

28. A system as in claim 24, wherein the catheter body further includes a pressure measurement lumen extending from the balloon to the proximal end, wherein the pressure measuring means comprises a pressure sensor disposed near the proximal end of the pressure measurement lumen.

29. A system for measuring an internal dimension of a body lumen, said system comprising:

a catheter body having a proximal end, a distal end, and an inflation lumen extending from the proximal end to near the distal end;

an inflatable balloon mounted near the distal end of the catheter body and being connected to the inflation lumen;

means for introducing a volume of an incompressible medium through a proximal end of the inflation lumen to inflate the inflatable balloon;

means for measuring the pressure of incompressible medium within the balloon; and means for calculating the internal dimension of a location within the body lumen based on the difference between (a) the volume of inflation medium required to produce a preselected pressure of inflation medium within the balloon when the balloon is unconstrained and (b) the volume of inflation medium required to produce the same pressure of inflation medium within the balloon when the balloon is at the location.

30. A system as in claim 29, wherein the catheter body includes at least a second lumen which is connected at its distal end to the interior of the inflatable balloon and wherein the means for measuring pressure is connected to said second lumen.

31. A system as in claim 29, wherein the means for measuring pressure comprises a pressure sensor disposed within the interior of the inflatable balloon.

32. A system as in claim 29, wherein the means for measuring pressure comprises a pressure sensor disposed at or near the proximal end of the inflation lumen.

33. A system for connection to a balloon catheter for determining a physiologic characteristic of a body lumen, said system comprising:

means for introducing a measured volume of incompressible fluid to the balloon catheter;

means for receiving a signal corresponding to static pressure within the balloon from the catheter; and means for calculating the physiologic characteristic based on the value of the measured volume of inflation medium at one or more measured pressures below 200 mmhg.

34. A system as in claim 33, wherein the means for introducing comprises a syringe operatively connected to a position controlled motor.

35. A system as in claim 33, wherein the means for calculating comprises a microprocessor which is connected to both the positioned controlled motor and the pressure means for receiving.

* * * * *